US012558042B2

(12) United States Patent
Horiuchi et al.

(10) Patent No.: US 12,558,042 B2
(45) Date of Patent: Feb. 24, 2026

(54) INFORMATION PROCESSING APPARATUS, IMAGE GENERATION SYSTEM, AND PROGRAM

(71) Applicant: FUJIFILM CORPORATION, Tokyo (JP)

(72) Inventors: Hisatsugu Horiuchi, Kanagawa (JP); Lisako Nobuyama, Kanagawa (JP); Koji Shimomura, Kanagawa (JP); Takeyasu Kobayashi, Kanagawa (JP); Sayaka Saito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/817,241

(22) Filed: Aug. 28, 2024

(65) Prior Publication Data

US 2025/0099048 A1 Mar. 27, 2025

(30) Foreign Application Priority Data

Sep. 22, 2023 (JP) ................................. 2023-158491

(51) Int. Cl.
| | |
|---|---|
| *A61B 6/04* | (2006.01) |
| *A61B 6/00* | (2024.01) |
| *A61B 6/50* | (2024.01) |
| *A61B 8/00* | (2006.01) |
| *A61B 8/08* | (2006.01) |
| *A61B 6/02* | (2006.01) |

(52) U.S. Cl.
CPC .......... *A61B 6/0414* (2013.01); *A61B 6/0435* (2013.01); *A61B 6/502* (2013.01); *A61B 6/5217* (2013.01); *A61B 6/5247* (2013.01);

*A61B 8/0825* (2013.01); *A61B 8/403* (2013.01); *A61B 8/406* (2013.01); *A61B 8/5223* (2013.01); *A61B 8/5261* (2013.01)

(58) Field of Classification Search
CPC ..... A61B 6/502; A61B 6/0414; A61B 8/0825; A61B 8/403
See application file for complete search history.

(56) References Cited

U.S. PATENT DOCUMENTS

| | | | |
|---|---|---|---|
| 11,701,069 B2 * | 7/2023 | Arai ..................... | A61B 6/0435 |
| | | | 600/445 |
| 2008/0087830 A1 * | 4/2008 | Kashiwagi ............. | A61B 5/103 |
| | | | 250/363.05 |
| 2012/0157819 A1 * | 6/2012 | Jerebko .................. | G16H 50/30 |
| | | | 600/407 |
| 2017/0132792 A1 * | 5/2017 | Jerebko .................. | G16H 50/30 |

(Continued)

FOREIGN PATENT DOCUMENTS

| | | |
|---|---|---|
| JP | 2006-305160 A | 11/2006 |
| JP | 2009-178185 A | 8/2009 |
| JP | 2016-059743 A | 4/2016 |

*Primary Examiner* — Colin T. Sakamoto

(74) *Attorney, Agent, or Firm* — SOLARIS Intellectual Property Group, PLLC

(57) ABSTRACT

A console includes an estimation unit that estimates, in a case where capturing of a radiation image and an ultrasound image is performed for a breast in a state of being compressed by a compression member, a property related to a lesion of the breast during non-compression by the compression member, based on a measurement result for the lesion in the state in which the breast is compressed by the compression member.

11 Claims, 13 Drawing Sheets

(56)          References Cited

U.S. PATENT DOCUMENTS

| | | | | |
|---|---|---|---|---|
| 2020/0323512 A1* | 10/2020 | Ng | .......................... | A61B 8/085 |
| 2020/0375562 A1* | 12/2020 | Arai | ....................... | A61B 8/403 |
| 2020/0397410 A1* | 12/2020 | Koshino | ............. | A61B 8/5261 |
| 2022/0096024 A1* | 3/2022 | Fujimoto | ............. | A61B 6/0414 |
| 2022/0101553 A1* | 3/2022 | Konno | ................. | G06T 7/0012 |
| 2023/0124481 A1* | 4/2023 | St. Pierre | .............. | G16H 40/67 |
| | | | | 600/427 |
| 2023/0309946 A1* | 10/2023 | Tsubota | .................. | A61B 6/54 |
| | | | | 378/37 |

* cited by examiner

52

CORRECTION COEFFICIENT DATABASE

| COMPRESSION PRESSURE (N) | COMPRESSION THICKNESS (mm) | CORRECTION COEFFICIENT | |
|---|---|---|---|
| | | HORIZONTAL DIRECTION (TIMES) | VERTICAL DIRECTION (TIMES) |
| 40 | 60 | 0.98 | 1.01 |
| | 50 | 0.96 | 1.03 |
| | ⋮ | ⋮ | ⋮ |
| 50 | 60 | 0.93 | 1.02 |
| | 50 | 0.92 | 1.04 |
| | ⋮ | ⋮ | ⋮ |
| ⋮ | ⋮ | ⋮ | ⋮ |

FIRST SIZE DISPLAY SCREEN

54

ULTRASOUND IMAGE OF BREAST

CROSS SECTION IN VERTICAL DIRECTION

DISTANCE: 27.7 mm (DURING NON-COMPRESSION: 28.2 mm)

CROSS SECTION IN HORIZONTAL DIRECTION

DISTANCE: 27.9 mm (DURING NON-COMPRESSION: 26.0 mm)

SIZE OF TUMOR DURING REDUCTION
OF COMPRESSION PRESSURE    52

| COMPRESSION PRESSURE (N) | MEASURED SIZE OF PROVISIONAL TUMOR (mm) |
|---|---|
| 50 | 10.5 |
| 40 | 10.4 |
| 30 | 10.3 |
| 20 | – |

FIRST SIZE DISPLAY SCREEN    54

TUMOR DIAMETER: 12 × 13 × 9 mm
(DURING NON-COMPRESSION: 11 × 12 × 10 mm)

SHAPE: LOBULAR SHAPE

FIG. 15

CORRECTION COEFFICIENT DATABASE

52

| COMPRESSION PRESSURE (N) | CORRECTION COEFFICIENT | |
| --- | --- | --- |
| | HORIZONTAL DIRECTION (TIMES) | VERTICAL DIRECTION (TIMES) |
| 40 | 0.98 | 1.01 |
| 50 | 0.93 | 1.02 |
| . . . | . . . | . . . |

INFORMATION PROCESSING APPARATUS, IMAGE GENERATION SYSTEM, AND PROGRAM

CROSS-REFERENCE TO RELATED APPLICATION

This application claims priority from Japanese Patent Application No. 2023-158491, filed Sep. 22, 2023, the disclosure of which is incorporated herein by reference in its entirety.

BACKGROUND

Technical Field

The present disclosure relates to an information processing apparatus, an image generation system, and a non-transitory computer-readable storage medium storing a program.

Related Art

JP2016-59743A discloses a medical image system that is intended to enable an examination implementer of an ultrasound examination to easily and accurately recognize a position corresponding to a region of interest on a medical image obtained in an X-ray examination in a subject site in a case where an X-ray examination and an ultrasound examination of the same subject site are performed as separate examinations.

The medical image system comprises a display unit that displays one or more medical images obtained by capturing a subject site with X-rays, a designation unit for designating a region of interest from the medical image, and a derivation unit that derives an amount of deformation of the subject site corresponding to a position of the region of interest in the medical image due to compression during capturing. In addition, the medical image system comprises an estimation unit that estimates a position of the region of interest when the subject site is viewed from the front based on an angle at which an X-ray imaging apparatus is tilted during the capturing of the medical image, the position of the region of interest in the medical image, and an amount of deformation of the subject site corresponding to the position of the region of interest due to the compression during the imaging, a generation unit that generates estimation clinical position information indicating the position of the region of interest when the subject site estimated by the estimation unit is viewed from the front, and a display controller that displays the generated estimation clinical position information on the display unit.

In addition, JP2009-178185A discloses a medical imaging apparatus that is used for capturing a mammary gland and a breast while compressing the breast with a compression plate, and that is intended to visualize an elastic property in a tissue to clarify a tumor portion.

The medical imaging apparatus comprises an imaging table on which a subject is placed, a compression plate that has a first surface for compressing the subject and a second surface facing the first surface and that compresses the subject between the compression plate and the imaging table, and a compression plate moving mechanism that moves the compression plate in a first direction substantially perpendicular to the first surface or in a second direction substantially parallel to the first surface. In addition, the medical imaging apparatus comprises a first unit that generates a signal by generating radiation or ultrasound wave and detecting radiation transmitted through the subject or the ultrasound wave reflected by the subject, and a second unit that generates an image signal representing an image of the subject based on the signal generated by the first unit while controlling the compression plate moving mechanism such that the compression plate compresses the subject in the first direction between the compression plate and the imaging table and controlling the compression plate moving mechanism such that the compression plate vibrates the subject in the second direction.

Further, JP2006-305160A discloses an ultrasound diagnostic apparatus that is intended to provide information on a degree of variation in displacement of each part of a living body with respect to a compression force to further improve accuracy or reliability of tissue differentiation.

The ultrasound diagnostic apparatus comprises a transmission unit that repeatedly scans a subject with an ultrasound beam, a reception unit that receives a reflected echo signal of the ultrasound wave from the subject, and a frame data acquisition unit that acquires frame data consisting of the reflected echo signal corresponding to a scanning surface of the ultrasound beam in a process in which a pressure in the subject changes. In addition, the ultrasound diagnostic apparatus comprises a displacement measurement unit that obtains a displacement at a plurality of measurement points on the scanning surface based on a pair of the frame data having different acquisition time points, a displacement variation image generation unit that generates a displacement variation image representing a degree of variation of the displacement at each of the measurement points, and a display unit that displays the displacement variation image.

Meanwhile, in a case where a breast is compressed by a compression member, a property of a lesion present in the breast changes as compared with that during non-compression.

However, in the technology described in each of JP2016-59743A, JP2009-178185A, and JP2006-305160A, there is a problem in which a difference in properties of lesions during compression and non-compression is not taken into consideration, and processing using the difference in the properties can not be performed.

SUMMARY

The present disclosure has been made in view of the above circumstances, and an object of the present disclosure is to provide an information processing apparatus, an image generation system, and a program that can perform processing using the difference in the properties of the lesions during compression and non-compression by a compression member.

In order to achieve the above-described object, an information processing apparatus according to a first aspect of the present disclosure comprises at least one processor, in which the processor estimates, in a case where capturing of a radiation image and an ultrasound image is performed for a breast in a state of being compressed by a compression member, a property related to a lesion of the breast during non-compression by the compression member, based on a measurement result for the lesion in the state in which the breast is compressed by the compression member.

There is provided the information processing apparatus according to a second aspect of the present disclosure, in the information processing apparatus according to the first aspect, in which the measurement result is a size of the lesion in the state in which the breast is compressed by the compression member, and the property is a size of the lesion during the non-compression.

There is provided the information processing apparatus according to a third aspect of the present disclosure, in the information processing apparatus according to the second aspect, in which the processor executes, in a case where the lesion is a tumor, processing of supporting category classification of the tumor by using the estimated size of the tumor during the non-compression.

There is provided the information processing apparatus according to a fourth aspect of the present disclosure, in the information processing apparatus according to the second aspect or the third aspect, in which the processor estimates the size of the lesion during the non-compression in three directions intersecting with each other.

There is provided the information processing apparatus according to a fifth aspect of the present disclosure, in the information processing apparatus according to the second aspect or the third aspect, in which the processor performs, in a case where the size of the lesion is equal to or larger than a predetermined threshold value, estimation of the size of the lesion during the non-compression.

There is provided the information processing apparatus according to a sixth aspect of the present disclosure, in the information processing apparatus according to the first aspect, the measurement result is a measurement result of how the lesion is deformed by changing a compression pressure by the compression member, and the property is at least one of a size of the lesion during the non-compression or a state indicating whether or not the lesion is a liquid.

There is provided the information processing apparatus according to a seventh aspect of the present disclosure, in the information processing apparatus according to the sixth aspect, in which the change in the compression pressure is performed at a position in which the lesion is suspected.

In addition, in order to achieve the above-described object, an image generation system according to an eighth aspect of the present disclosure comprises the information processing apparatus according to the first aspect and an image generation apparatus that generates an image used in the information processing apparatus.

In addition, in order to achieve the above-described object, a non-transitory computer-readable storage medium storing a program according to a ninth aspect of the present disclosure causing a computer to execute a process comprises estimating a property related to a lesion of the breast during non-compression by a compression member, based on a measurement result for the lesion in a state in which the breast is compressed by the compression member, in a case where capturing of a radiation image and an ultrasound image is performed for the breast in a state of being compressed by the compression member.

According to the present disclosure, processing using a difference in properties of lesions during the compression and the non-compression by the compression member can be performed.

BRIEF DESCRIPTION OF THE DRAWINGS

FIG. 15 is a schematic diagram showing an example of a configuration of a correction coefficient database according to a modification example of the embodiment.

DETAILED DESCRIPTION

Hereinafter, a description of embodiments of the present disclosure will be made with reference to the accompanying drawings.

First Embodiment

Figure 1:
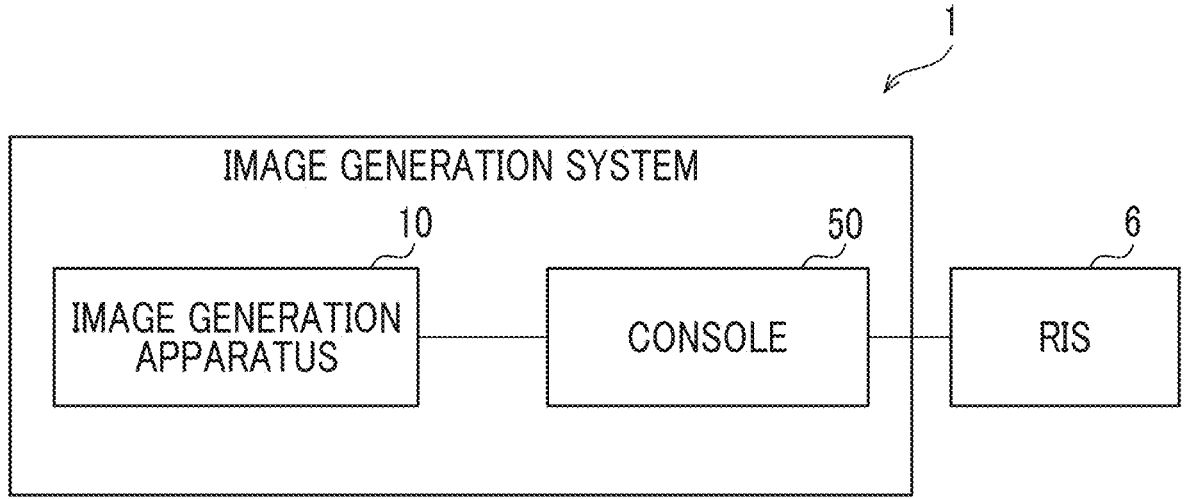
FIG. 1 is a diagram showing an example of a schematic configuration of an image generation system according to an embodiment.

First, a description of a configuration of an image generation system 1 to which the technology of the present disclosure is applied will be made with reference to FIG. 1. FIG. 1 is a view showing an example of a schematic configuration of the image generation system 1 according to the present embodiment.

As shown in FIG. 1, the image generation system 1 comprises an image generation apparatus 10 and a console 50. The image generation apparatus 10 and the console 50, and the console 50 and an external radiology information system (RIS) 6 are configured to be connected to each other via a wired or wireless network.

In the image generation system 1 according to the present embodiment, the console 50 acquires an imaging order or the like from the RIS 6, and controls the image generation apparatus 10 in accordance with the imaging order, an instruction from the user, and the like. The image generation apparatus 10 captures a radiation image by irradiating a breast put into a compressed state between an imaging table 16 and a compression member 40, which will be described below, with radiation R. In addition, the image generation apparatus 10 acquires an ultrasound image of the breast put into the compressed state via the compression member 40.

Figure 2:
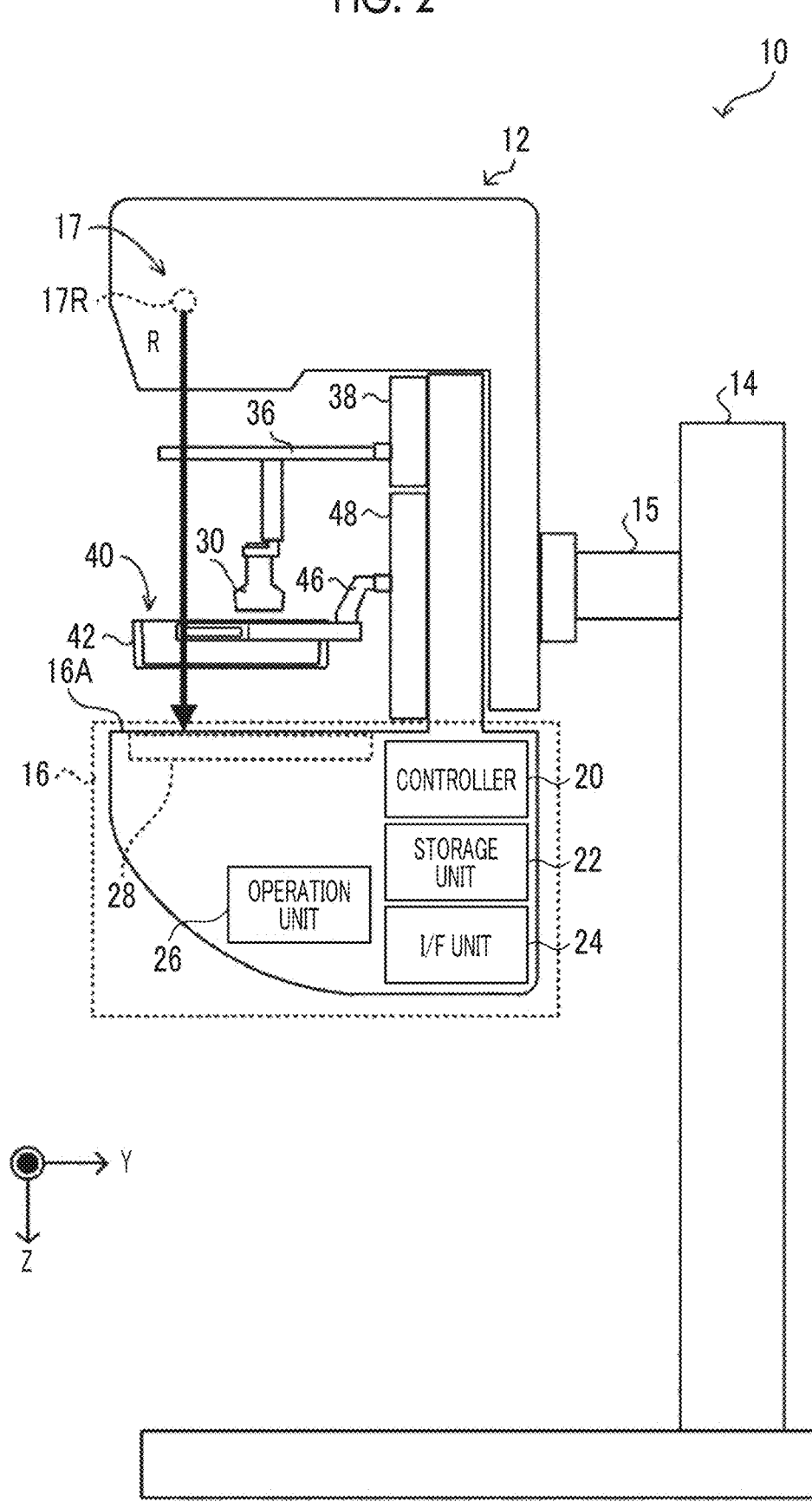
FIG. 2 is a side view showing an example of an appearance of the image generation apparatus according to the embodiment.

Next, a description of a schematic configuration of the image generation apparatus 10 according to the present embodiment will be made with reference to FIG. 2. FIG. 2 is a side view showing an example of an appearance of the image generation apparatus 10 according to the present embodiment, and is a view in a case where the image generation apparatus 10 is viewed from a right side of a subject. As shown in FIG. 2, the image generation apparatus 10 comprises a radiation source 17R, a radiation detector 28, the imaging table 16 disposed between the radiation source 17R and the radiation detector 28, the compression member 40 that compresses the breast between the compression member 40 and the imaging table 16, and an ultrasound probe 30. In the image generation apparatus 10, a user, such as a doctor or a technician, positions the breast of the subject on an imaging surface 16A of the imaging table 16.

The image generation apparatus 10 comprises an arm part 12, a base 14, and a shaft part 15. The arm part 12 is movably held in the vertical direction (Z direction) by the base 14. The shaft part 15 connects the arm part 12 to the base 14. The arm part 12 is rotatable relative to the base 14 with the shaft part 15 as a rotation axis. In addition, the arm part 12 may be relatively rotatable with respect to the base 14 with the shaft part 15 as the rotation axis separately between an upper part comprising a radiation emitting unit 17 and a lower part comprising the imaging table 16.

The arm part 12 comprises the radiation emitting unit 17 and the imaging table 16. The radiation emitting unit 17 comprises the radiation source 17R and is configured to change an irradiation field of radiation (for example, X-rays) emitted from the radiation source 17R. For example, the change of the irradiation field may be performed by the user operating an operation unit 26 or may be performed by a control unit 20 in accordance with a type of the attached compression member 40.

The imaging table 16 comprises the control unit 20, a storage unit 22, an interface (I/F) unit 24, the operation unit 26, and the radiation detector 28. The controller 20 controls an overall operation of the image generation apparatus 10 in accordance with the control of the console 50. The control unit 20 comprises a central processing unit (CPU), a read only memory (ROM), a random access memory (RAM), and the like (not shown). The ROM stores in advance various programs including a program executed by the CPU for performing the control related to the generation of the radiation image and the ultrasound image. The RAM transitorily stores various types of data.

Data of the radiation image and the ultrasound image, various types of other information, and the like are stored in the storage unit 22. The storage unit 22 is realized by, for example, a storage medium, such as a hard disk drive (HDD), a solid state drive (SSD), and a flash memory.

The I/F unit 24 communicates various types of information with the console 50 by wired communication or wireless communication. Specifically, the I/F unit 24 receives information related to the control of the image generation apparatus 10 from the console 50. In addition, the I/F unit 24 transmits the data of the radiation image and the ultrasound image to the console 50.

The operation unit 26 is a part provided on the imaging table 16 or the like and operable by the user with a hand, a foot, or the like, and is, for example, a switch, a button, a touch panel, or the like.

The radiation detector 28 is disposed inside the imaging table 16, detects the radiation R transmitted through the breast and the imaging table 16, generates the radiation image based on the detected radiation R, and outputs image data indicating the generated radiation image. It should be noted that a type of the radiation detector 28 is not particularly limited and may be, for example, an indirect conversion type radiation detector that converts the radiation R into light and converts the converted light into a charge, or may be a direct conversion type radiation detector that directly converts the radiation R into a charge.

Further, a probe unit 38 and a compression unit 48 are connected to the arm part 12. A support part 36 that attachably and detachably supports the ultrasound probe 30 is attached to the probe unit 38. The support part 36 (ultrasound probe 30) is moved in the vertical direction and the horizontal direction (X direction, Y direction, and Z direction) by a driving unit (not shown) provided in the probe unit 38. The support part 36 is preferably formed of a material that transmits the radiation R.

The ultrasound probe 30 is used for obtaining the ultrasound image of the breast put into the compressed state by the compression member 40, is disposed between the radiation source 17R and the compression member 40, irradiates the breast with ultrasound waves via the compression member 40, and receives reflected waves from the breast. Further, the probe unit 38 includes a converter (not shown) that converts the reflected waves from the breast received by the ultrasound probe 30 into the ultrasound image, and the ultrasound image is obtained by the converter.

Specifically, the ultrasound probe 30 comprises an ultrasound transducer array. The ultrasound transducer array has a configuration in which a plurality of ultrasound transducers are arranged one-dimensionally or two-dimensionally. The ultrasound transducer may be constituted, for example, by forming electrodes at both ends of a piezoelectric body such as a piezoelectric ceramic represented by lead zirconate titanate (PZT), a piezoelectric single crystal represented by lead magnesium niobate-lead titanate (PMN-PT), and a polymer piezoelectric element represented by polyvinylidene difluoride (PVDF). Further, for example, the ultrasound transducer may be a capacitive micro-machined ultrasound transducer (CMUT).

In addition, a plurality of types of the ultrasound probes 30 different from each other may be interchangeably attached to the image generation apparatus 10. Specifically, in accordance with a physique of the subject (for example, a size of the breast), a tissue composition of the breast (for example, a fat mass and a mammary gland mass), a type of imaging (for example, magnified imaging and spot imaging), and the like, the ultrasound probes 30 each having different performances and dimensions may be attached. For example, a linear probe having a center frequency of about 7.5 MHz (for superficial use, or the like), a convex probe having a center frequency of about 3.5 MHz (for abdomen, or the like), a sector probe having a center frequency of about 2.5 MHz (for heart, or the like), and the like may be used.

A support part 46 that supports the compression member 40 is attachably and detachably attached to the compression unit 48. The support part 46 (compression member 40) is moved in the vertical direction (Z direction) by a driving unit (not shown) provided in the compression unit 48.

Figure 3:
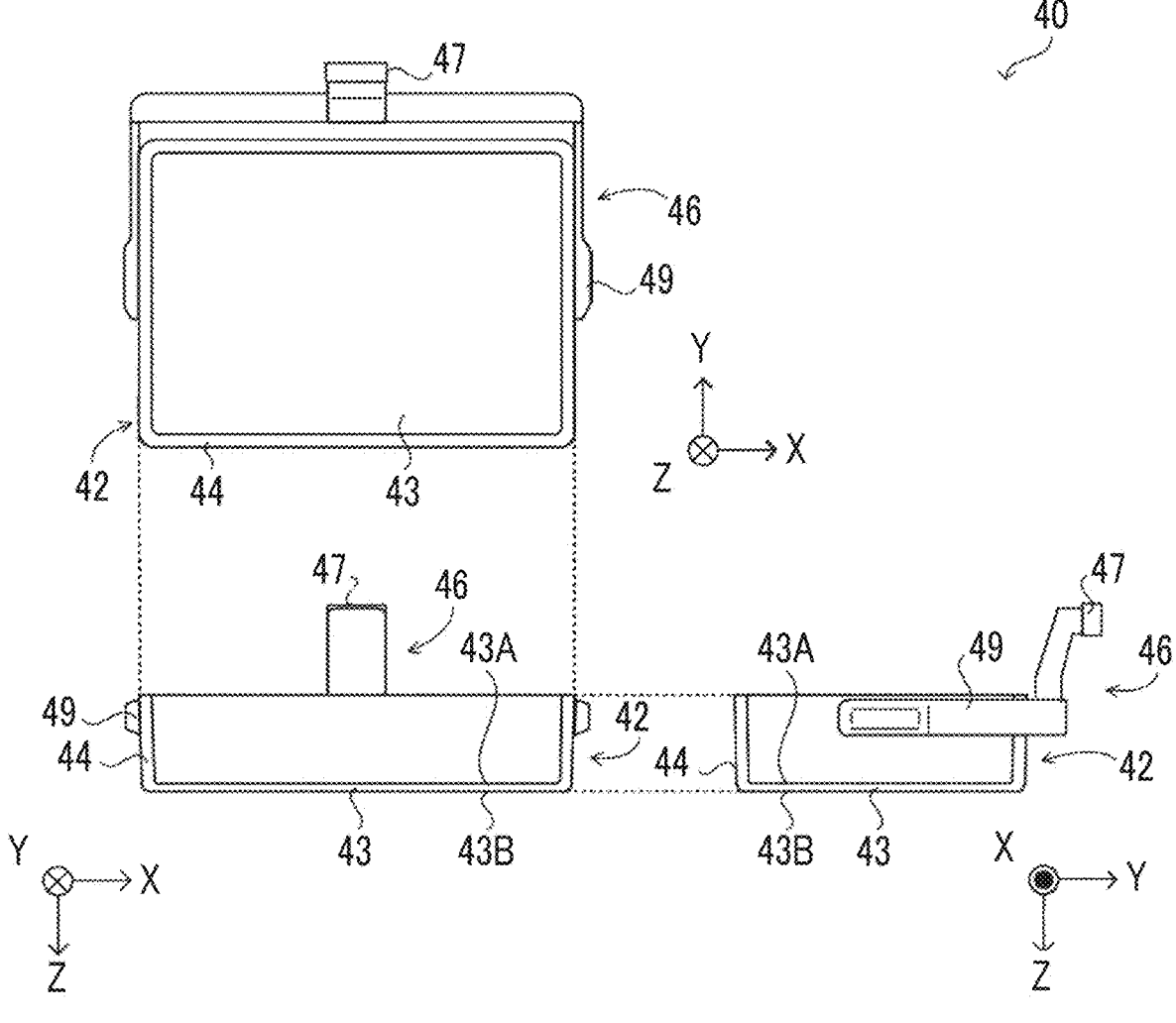
FIG. 3 is a three-view showing an example of a schematic configuration of a compression member according to the embodiment.

The compression member 40 is disposed between the radiation source 17R and the imaging table 16 and sandwiches the breast between the compression member 40 and the imaging table 16 to put the breast into a compressed state. FIG. 3 shows a three-view of an example of the compression member 40. The three-view of FIG. 3 includes a top view of the compression member 40 as viewed from above (radiation emitting unit 17 side), a side view thereof as viewed from the subject side, and a side view thereof as viewed from the right side of the subject. As shown in FIG. 3, the compression member 40 includes a compression part 42 and the support part 46.

The support part 46 includes an attachment portion 47 and an arm 49. The attachment portion 47 attaches the compression member 40 to the image generation apparatus 10, specifically, the driving unit of the compression unit 48. The arm 49 supports the compression part 42.

In the compression part 42, a bottom portion 43 configured to be substantially flat is surrounded by a wall portion 44 having a substantially uniform height and a cross-sectional shape is formed in a recessed shape. The compression part 42 is preferably formed of an optically transparent or translucent material in order to perform positioning and confirmation of a compressed state in compression of the breast. In addition, the compression part 42 is preferably formed of a material excellent in transmittance of the radiation R and ultrasound waves. Further, the compression part 42 is preferably formed of, for example, a material excellent in strength such as drop strength and compression strength.

As such a material, for example, a resin such as polymethylpentene (PMP), polycarbonate (PC), acryl, polypropylene (PP), and polyethylene terephthalate (PET) can be used. In particular, in the polymethylpentene, acoustic impedance, which affects transmissivity and reflectivity of ultrasound waves, is close to that of a human body (breast) as compared with other materials, and a proportion of noise on the ultrasound image can be reduced. Therefore, the polymethylpentene is suitable as the material for the compression part 42.

In addition, a plurality of types of the compression members 40 different from each other may be interchangeably attached to the image generation apparatus 10. Specifically, in accordance with a physique of the subject (for example, a size of the breast), a tissue composition of the breast (for example, a fat mass and a mammary gland mass), a type of imaging (for example, magnified imaging and spot imaging), and the like, the compression members 40 having different materials, sizes, and shapes from each other may be attached. For example, a compression member in accordance with the size of the breast, a compression member for axillary imaging, a compression member for magnified imaging, and a compression member for so-called spot imaging that captures a radiation image of only a region where a lesion exists, and the like may be used. That is, the compression member 40 is not limited to the one that compresses the entire breast, and may be smaller than the breast that seems to compress a part of the breast.

Figure 4:
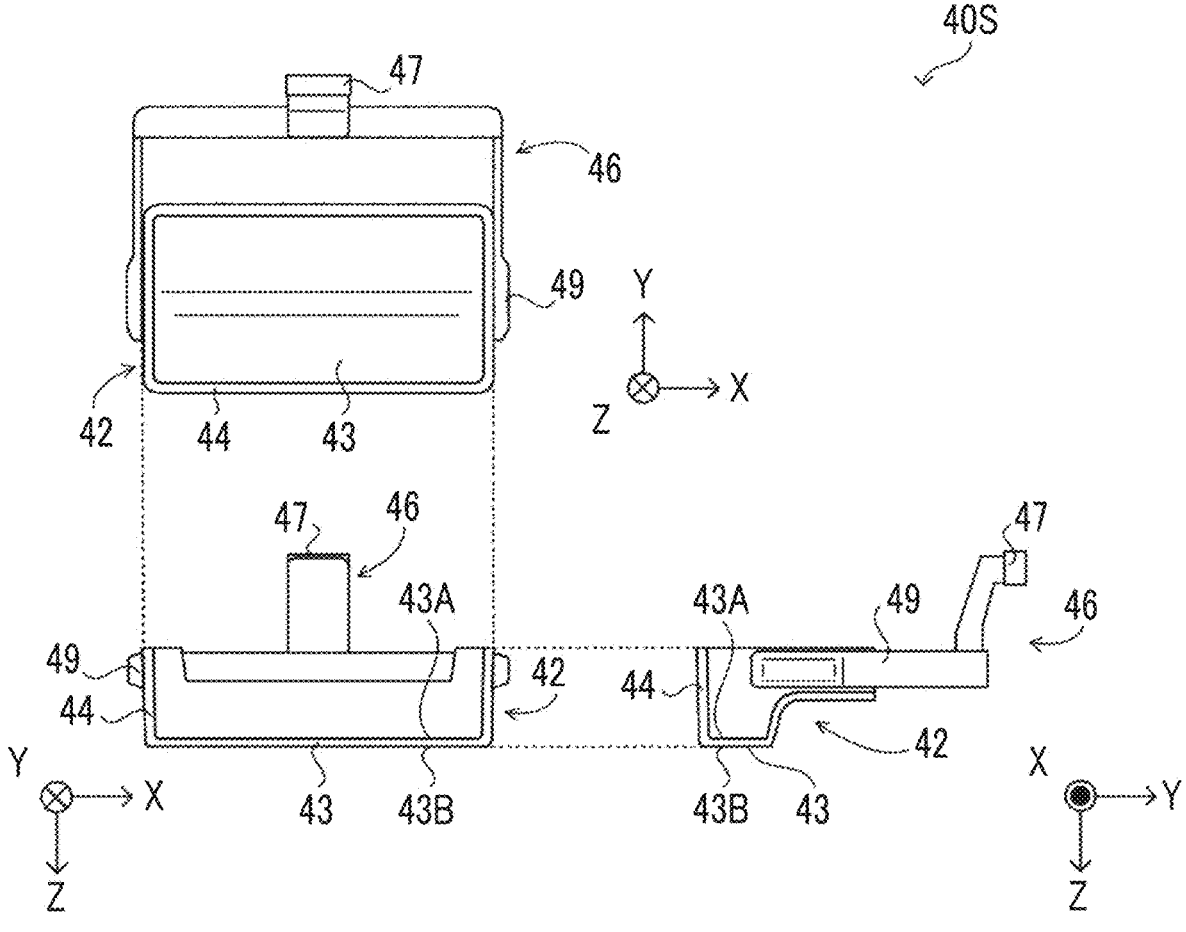
FIG. 4 is a three-view showing an example of the schematic configuration of the compression member according to the embodiment.

FIG. 4 shows a three-view of the compression member 40S for a small breast as an example of another form different from the compression member 40 of FIG. 3. The three-view of FIG. 4 includes a top view of the compression member 40S as viewed from above (the radiation emitting unit 17 side), a side view thereof as viewed from the subject side, and a side view thereof as viewed from the right side of the subject. The compression member 40S includes the compression part 42 and the support part 46, similarly to the compression member 40 in FIG. 3. In the compression member 40S, the bottom portion 43 is not flat, and the attachment portion 47 side is higher than a chest wall side (side away from attachment portion 47). In addition, a height of the wall portion 44 is not uniform, and a height of a part of the chest wall side is lower than a height of other portions. Due to such a shape, the compression member 40S can easily perform positioning and compression even in a small breast.

As described above, in the image generation apparatus 10, at least one of the compression member 40 for putting the breast into the compressed state or the ultrasound probe 30 for acquiring the ultrasound image can be attached and detached. In this case, the image generation apparatus 10 may detect the types of the compression member 40 and the ultrasound probe 30 that are attached.

For example, the attachment portion 47 of the compression member 40 may be provided with a plurality of pins having different dispositions for each type of the compression member 40 as identification information, and the identification information may be read by a sensor (for example, a photointerrupter) capable of detecting the disposition of the pins provided in the compression unit 48. Further, for example, a marker (for example, a bar code, a two-dimensional code, or the like) corresponding to the type of the compression member 40 may be provided at any position of the compression member 40 as identification information, and the identification information may be read by a sensor (for example, a charge coupled device (CCD) sensor or the like) capable of detecting the marker.

Further, for example, a radio frequency identification (RFID) tag having identification information corresponding to the type of the compression member 40 may be provided at any position of the compression member 40 and the identification information may be read by an RFID reader capable of reading the RFID tag. Further, for example, a weight of each type of the compression member 40 and the identification information may be stored in the storage unit 22 in advance in association with each other, a weight of the attached compression member 40 may be measured by a sensor capable of detecting the weight, and the identification information (type of the compression member 40) may be specified based on a measured value.

Similarly, for the ultrasound probe 30, the type of the attached ultrasound probe 30 may be identified in accordance with, for example, a pin, a marker, an RFID tag, a weight, or the like.

In addition, the image generation apparatus 10 detects a compression pressure applied to the breast by the compression member 40. For example, in a case where the compression member 40 compresses the breast, a reaction force equal to the compression pressure is applied to the driving unit of the compression member 40. Using this, a strain gauge (for example, a load cell or the like) for detecting the reaction force applied to the driving unit may be provided in the compression unit 48, and the reaction force detected by the strain gauge may be detected as the compression pressure. Further, for example, the compression pressure may be detected by using a semiconductor pressure sensor, a capacitive pressure sensor, and the like. Further, for example, various sensors for detecting the compression pressure may be provided on the compression member 40 side instead of the compression unit 48 side.

In addition, the image generation apparatus 10 detects a distance between the imaging surface 16A of the imaging table 16 and a contact surface 43B of the bottom portion 43 of the compression part 42 in the compression member 40 in a case where the compression member 40 compresses the breast (hereinafter, referred to as "compression thickness"). For example, a distance sensor using laser light, ultrasound waves, or the like may be used to detect the compression thickness. In addition, a form may be adopted in which the compression thickness is detected from a position of the support part 46 in the vertical direction.

It should be noted that a gel-like or liquid-like medium having ultrasound transmittance may be applied to an upper surface 43A of the bottom portion 43 of the compression member 40 and/or the contact surface 43B with the breast. As such a medium, for example, a known jelly for an ultrasound examination, which has the acoustic impedance close to the acoustic impedance of the human body (breast), can be applied. That is, the image generation apparatus 10 may acquire the ultrasound image of the breast put into the compressed state by the compression member 40 in a state of being applied with the gel-like or liquid-like medium having the ultrasound transmittance, via the compression member 40. In this case, it is possible to suppress entry of air into an interface between an ultrasound radiation surface of the ultrasound probe 30 and the upper surface 43A and/or an interface between the contact surface 43B and the breast, and it is possible to reduce a difference in acoustic impedance at each interface, so that the proportion of the noise applied to the ultrasound image can be decreased.

In addition, the method of imaging the breast via the image generation apparatus 10 is not particularly limited. For example, cranio-caudal (CC) imaging, medio-lateral oblique (MLO) imaging, magnified imaging and spot imaging for imaging a part of the breast, and the like may be performed. The CC imaging is a method of imaging the breast in a compressed state by sandwiching the breast between the imaging table 16 and the compression member 40 in the vertical direction (Z direction). The MLO imaging is a method of imaging the breast in a compressed state including an axillary portion by sandwiching the breast between the imaging table 16 and the compression member 40 in a tilted state in which a rotation angle of the arm part 12 with respect to the base 14 is equal to or more than 45 degrees and less than 90 degrees.

In addition, for example, the image generation apparatus 10 may perform tomosynthesis imaging. In the tomosynthesis imaging, the radiation R is emitted from each of a plurality of irradiation positions having different irradiation angles toward the breast by the radiation source 17R, and a plurality of radiation images of the breast are captured. That is, in the tomosynthesis imaging, the imaging is performed by changing a rotation angle of the radiation emitting unit 17 with respect to the base 14 while keeping angles of the imaging table 16, the compression member 40, the breast, and the like.

In addition, in the image generation apparatus 10, the breast of the subject may be positioned not only in a state in which the subject is standing (standing state) but also in a state in which the subject is sitting on a chair, a wheelchair, or the like (sitting state).

The console 50 sets an upper limit value of the compression pressure applied to the breast by the compression member 40 in accordance with the type of the compression member 40 attached to the image generation apparatus 10. In addition, the console 50 controls the image generation apparatus 10 to acquire the radiation image in accordance with the imaging order acquired from the RIS 6, the instruction from the user, and the like. In addition, the console 50 controls a position of the ultrasound probe 30 so that the ultrasound image can be acquired in accordance with a position of a region of interest included in the radiation image captured in the image generation apparatus 10.

As described above, the image generation apparatus 10 according to the present embodiment is provided with the probe unit 38 between the radiation emitting unit 17 and the compression unit 48, and can acquire both the radiation image and the ultrasound image while the breast is put into the compressed state by the compression member 40. Accordingly, a differential determination ability of a lesion can be improved by facilitating the registration between these images, displaying both images in a state of being superimposed on each other, or by performing similar steps.

Next, a description of the console 50 according to the present embodiment will be made.

Figure 5:
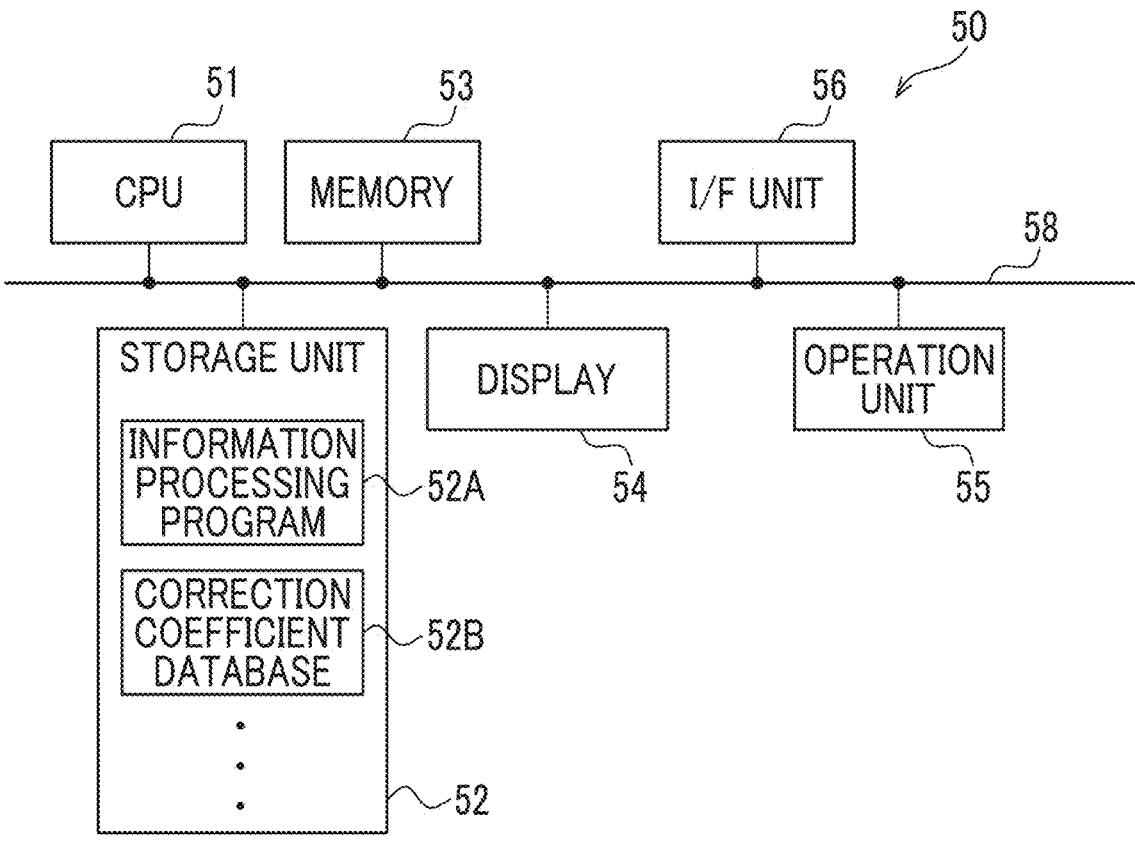
FIG. 5 is a block diagram showing an example of a hardware configuration of a console according to the embodiment.

An example of a hardware configuration of the console 50 will be described with reference to FIG. 5. As shown in FIG. 5, the console 50 includes a CPU 51, a non-volatile storage unit 52, and a memory 53 as a temporary storage area. In addition, the console 50 includes a display 54 such as a liquid crystal display, an operation unit 55 such as a touch panel, a keyboard, and a mouse, and an I/F unit 56. The I/F unit 56 performs wired or wireless communication with the image generation apparatus 10, the RIS 6, other external apparatuses, and the like. The CPU 51, the storage unit 52, the memory 53, the display 54, the operation unit 55, and the I/F unit 56 are connected to each other via a bus 58 such as a system bus and a control bus such that various types of information can be exchanged.

The storage unit 52 is realized by, for example, a storage medium such as an HDD, an SSD, and a flash memory. An information processing program 52A is stored in the storage unit 52. The CPU 51 reads the information processing program 52A from the storage unit 52, develops the information processing program 52A into the memory 53, and executes the developed information processing program 52A. As the console 50, for example, a personal computer, a server computer, a smartphone, a tablet terminal, a wearable terminal, or the like can be appropriately applied.

In addition, the storage unit 52 stores a correction coefficient database 52B. Details of the correction coefficient database 52B will be described below.

Further, the storage unit 52 stores the image data of the radiation image and the ultrasound image acquired by the image generation apparatus 10, various types of other information, and the like. The image data of the radiation image and the ultrasound image may be stored in association with at least one of an imaging order or imaging information. The imaging information may include, for example, at least one of subject information and an imaging item that are included in the imaging order, photographer information indicating a photographer (for example, a user such as a doctor or a technician) who performed the imaging, or date and time information indicating date and time when the imaging was performed.

Figure 6:
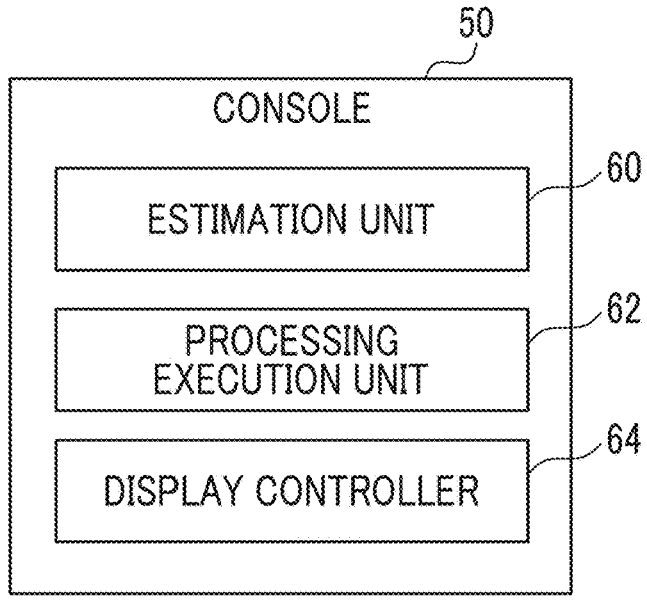
FIG. 6 is a block diagram showing an example of a functional configuration of the console according to the embodiment.

Next, an example of a functional configuration of the console 50 will be described with reference to FIG. 6. As shown in FIG. 6, the console 50 includes an estimation unit 60, a processing execution unit 62, and a display controller 64. The CPU 51 executes the information processing program 52A to function as the estimation unit 60, the processing execution unit 62, and the display controller 64.

The estimation unit 60 according to the present embodiment estimates, in a case where capturing of a radiation image and an ultrasound image is performed for a breast in a state of being compressed by the compression member 40, a property related to a lesion of the breast during the non-compression (hereinafter, also simply referred to as "during non-compression") by the compression member 40 based on a measurement result for the lesion in the state (hereinafter, also referred to as "during compression") in which the breast is compressed by the compression member 40. Further, the display controller 64 according to the present embodiment controls the display 54 to display a screen in accordance with the estimation result by the estimation unit 60. It should be noted that, in the present embodiment, the tumor is applied as a target lesion, but the present disclosure is not limited thereto. For example, a form may be adopted in which various lesions excluding tumors such as calcification and specula are applied as the target lesion.

Meanwhile, developers of the technology of the present disclosure have found that the size of the lesion during the compression is larger in the horizontal direction (direction intersecting direction in which compression pressure is applied) and is smaller in the vertical direction (direction in which compression pressure is applied) as the compression pressure on the breast increases, as compared with the size of the lesion during the non-compression.

Therefore, in the present embodiment, the size of the lesion during the compression is applied as the above-described measurement result, and the size of the lesion during the non-compression is applied as the above-described property. That is, the estimation unit 60 according to the present embodiment estimates the size of the lesion during the non-compression based on the size of the lesion of the breast during the compression. In the present embodiment, in order to estimate the size of the lesion during the non-compression, a correction coefficient is applied, which is described in detail below and can be multiplied by the size of the lesion measured during the compression to obtain the size of the lesion during the non-compression.

Figure 7:
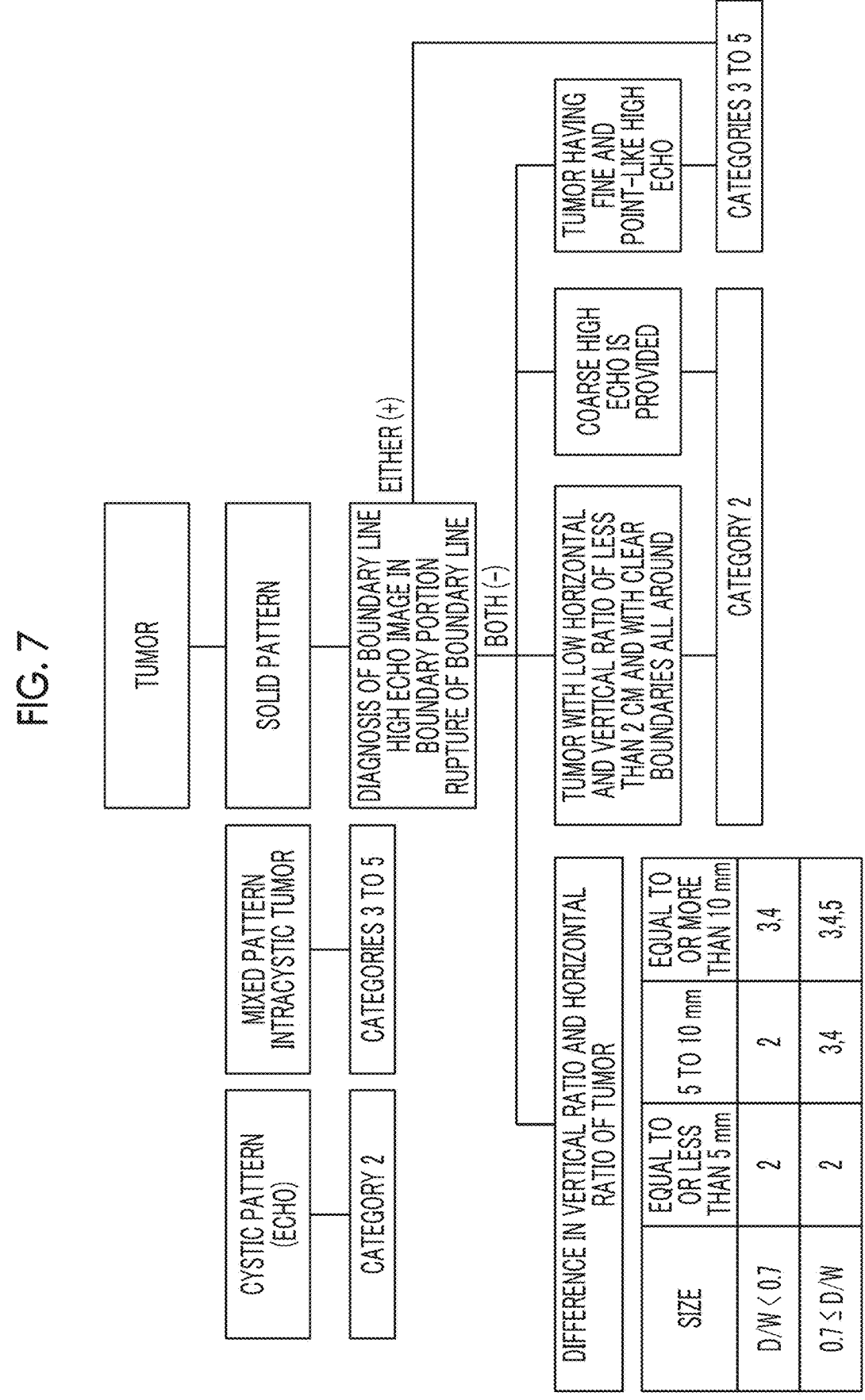
FIG. 7 is a schematic diagram showing a description of category classification of a tumor according to the embodiment.

In addition, the processing execution unit 62 according to the present embodiment executes, in a case where the lesion is a tumor, processing (hereinafter, referred to as "category classification support processing") of supporting category classification of the tumor by using the estimated size of the tumor during the non-compression. That is, currently, the category classification of the tumor is performed in a case where the tumor is detected in the breast according to the schematic diagram shown in FIG. 7 as an example. FIG. 7 is a schematic diagram showing a description of the category classification of the tumor according to the present embodiment, and is derived from "The Japan Association of Breast and Thyroid Sonology (JABTS) edition, ultrasound guidelines "Benign and malignant determination from US findings of mass forming lesions".

The category of the tumor is classified into five stages of category 1 to category 5, and the categories are distinguished as follows: category 1 is normal, category 2 is benign, category 3 is benign but malignancy cannot be denied (probability of cancer is 5% to 10%), category 4 is suspected to be malignant (probability of cancer is 30% to 50%), and category 5 is malignant (probability of cancer is almost 100%).

The estimation unit 60 according to the present embodiment estimates the size of the lesion during the non-compression as described above. Therefore, the processing execution unit 62 according to the present embodiment executes, in a case where the lesion is a tumor, the category classification support processing according to the category classification shown in FIG. 7 as an example, by using the size of the tumor estimated by the estimation unit 60.

It should be noted that, as shown in FIG. 7 as an example, in order to perform the category classification of the tumor, it is also necessary to have items that require determination by the doctor, such as a rupture condition of a boundary line of the tumor. Therefore, in the category classification support processing according to the present embodiment, the doctor is caused to input the item to determine a final category.

In addition, in the present embodiment, as the measurement result, a measurement result of how the lesion is deformed by changing the compression pressure by the compression member 40 is also applied, and as the property, a state indicating whether or not the lesion is a liquid is also applied. Further, in the present embodiment, the change in the compression pressure is performed at a position in which the lesion is suspected.

That is, since the tumor is filled with cells, rigidity is relatively high. On the other hand, for example, a liquid such as a cyst has a characteristic of lower rigidity than that of the tumor. Therefore, the estimation unit 60 according to the present embodiment estimates the rigidity of the lesion from the deformation (in present embodiment, amount of change in size of lesion) of the lesion when the compression pressure by the compression member 40 is changed, and estimates whether or not the lesion is the liquid or the tumor in accordance with the rigidity.

It should be noted that, in the estimation unit 60 according to the present embodiment, in a case where the size of the lesion is equal to or larger than a predetermined threshold value, the estimation of the size of the lesion during the non-compression is performed. That is, as a result of intensive studies by the developers of the technology of the present disclosure, it has been found that the amount of change in the size of the lesion from during the non-compression to during the compression is larger as the lesion is larger. Therefore, the estimation unit 60 according to the present embodiment performs estimation of the size of the lesion during the non-compression from the size of the lesion during the compression only in a case where the size (in present embodiment, larger size out of size in horizontal direction and size in vertical direction) of the lesion is equal to or larger than the predetermined threshold value.

Here, as an example, as shown in FIG. 7, a matter of concern in a case where the lesion is a tumor may be in a range from category 3 to category 5, and from a point that the size of the tumor during the non-compression is equal to or more than 5 mm, in the present embodiment, 5 mm is applied as the above-described threshold value, but the present disclosure is not limited thereto. For example, a form may be adopted in which the user is caused to appropriately input the threshold value in accordance with a condition of the image generation apparatus 10, a condition of the subject, or the like.

Figure 8:
FIG. 8 is a schematic diagram showing an example of a configuration of a correction coefficient database according to a first embodiment.

Next, the correction coefficient database 52B according to the present embodiment will be described with reference to FIG. 8. FIG. 8 is a schematic diagram showing an example of a configuration of the correction coefficient database 52B according to the present embodiment.

The correction coefficient database 52B according to the present embodiment is a database in which information indicating the correction coefficient described above is registered, and is used in a case where the size of the lesion during the non-compression is estimated from the size of the lesion during the compression. As shown in FIG. 8 as an example, in the correction coefficient database 52B according to the present embodiment, each information on the compression pressure, on the compression thickness, and on the correction coefficient is stored in association with each other.

The compression pressure and the compression thickness are information indicating the above-described compression pressure and compression thickness, respectively. The correction coefficient is information representing a coefficient for converting a size of a lesion (in present embodiment, tumor) into a size during the non-compression in a case where a compressed state with respect to the breast by the compression member 40 enters to the corresponding compression pressure and compression thickness.

As shown in FIG. 8, in the present embodiment, the correction coefficient is registered to correspond to two directions of the horizontal direction and the longitudinal direction of the tumor. For example, in a case where the compression pressure on the breast is 40 N and the compression thickness is 60 mm, a size during the non-compression in the horizontal direction and the vertical direction can be obtained by multiplying the size of the tumor in the horizontal direction by 0.98 and multiplying the size in the vertical direction by 1.01.

In the image generation system 1 according to the present embodiment, in order to obtain the correction coefficient to be registered in the correction coefficient database 52B, for example, sizes of the tumor during the compression and the non-compression of the actual breast obtained in the past in the horizontal direction and the vertical direction tis accumulated, and these values are used to obtain the correction coefficients for each direction.

Figure 9:
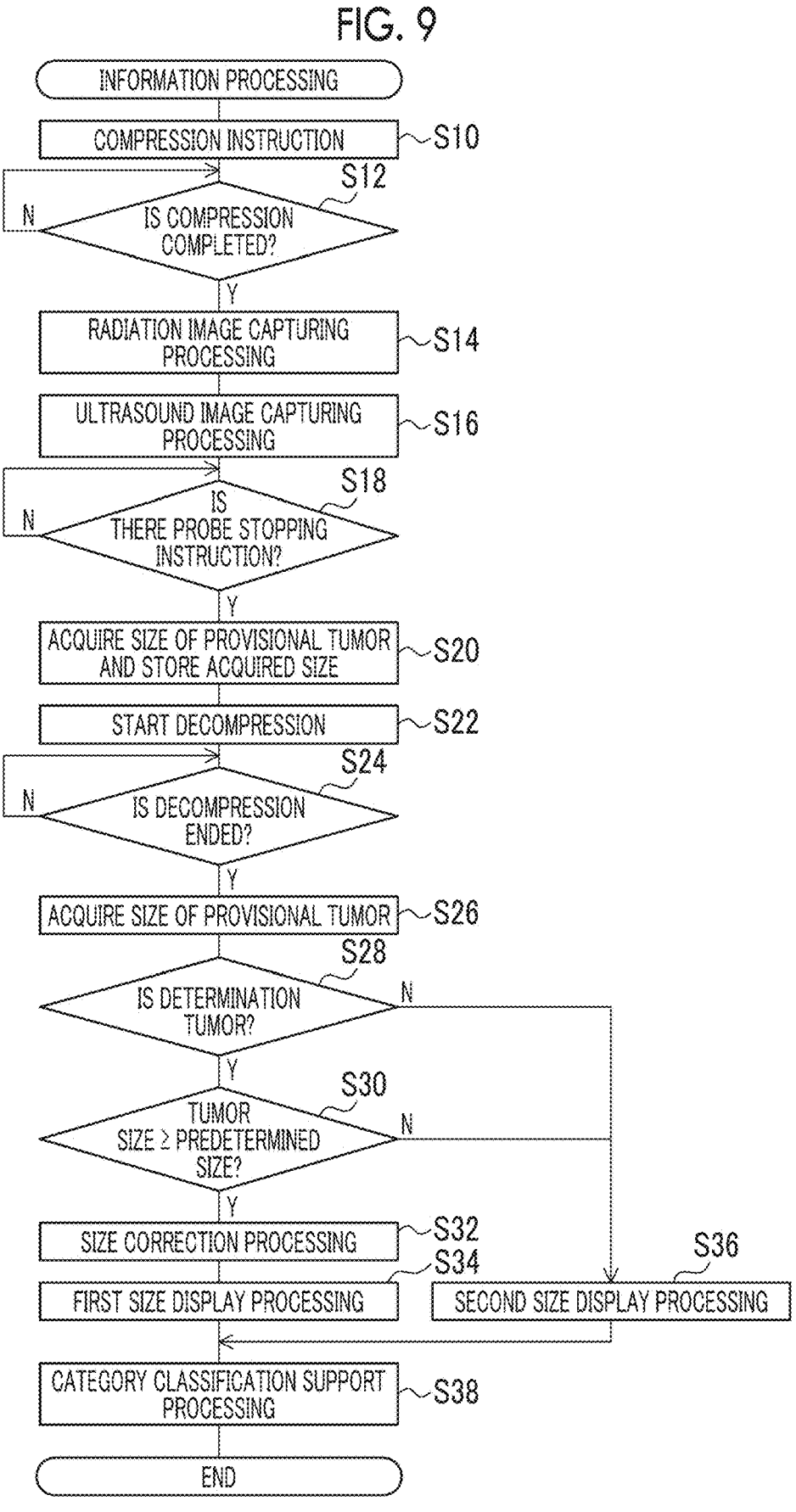
FIG. 9 is a flowchart showing an example of information processing according to the first embodiment.

Next, an action of the console 50 according to the present embodiment will be described with reference to FIG. 9. In the console 50, the CPU 51 executes the information processing program 52A to execute information processing shown in FIG. 9. This information processing is executed, for example, in a case where the user gives an instruction to start execution via the operation unit 55. It should be noted that, here, in order to avoid the complication, a case will be described in which the correction coefficient database 52B has already been constructed and the information (hereinafter, referred to as "setting information") indicating the compression pressure and the compression thickness during capturing of the radiation image of the breast is acquired from the RIS by the console 50. In addition, here, a case will be described in which the breast (hereinafter, referred to as "target breast") of the subject is positioned on the imaging surface 16A of the imaging table 16 by a user such as a doctor or a technician, the appropriate ultrasound probe 30 is mounted on the probe unit 38, and the ultrasound probe 30 is positioned at an initial position at a start of a predetermined scan (in present embodiment, horizontal movement).

In step S10, the CPU 51 gives an instruction to the image generation apparatus 10 such that the compression pressure and the compression thickness by the compression member 40 are set to values indicated by the setting information, so that the CPU gives an instruction to start the compression by the compression member 40 on the target breast. In step S12, the CPU 51 waits until the compression of the target breast by the compression member 40 is completed (compression pressure and compression thickness are set to the values indicated by the setting information). As a result of the above-described processing, the compressed state by the compression member 40 with respect to the target breast is set to a state during the compression.

In step S14, the CPU 51 controls the image generation apparatus 10 to capture the radiation image. With this control, the image generation apparatus 10 captures the radiation image of the target breast in which the compressed state by the compression member 40 is set to the state indicated by the setting information, and generates image data indicating the radiation image obtained by the imaging. As described above, various types of information required for capturing the radiation image in this case are acquired from the RIS.

In step S16, the CPU 51 controls the image generation apparatus 10 to capture the ultrasound image. With this control, the image generation apparatus 10 starts the scanning by the ultrasound probe 30, and starts the capturing of the ultrasound image and a real-time display of the ultrasound image obtained by the imaging on the display 54. In accordance with this display, with reference to the displayed ultrasound image, in a case where the position of the ultrasound probe 30 is set to a position to be noted, such as a position at which an object (hereinafter, referred to as "provisional tumor") with a high possibility of being the tumor in the ultrasound image is reflected in a center portion, the user inputs instruction information for instructing of stopping the scanning of the ultrasound probe 30 via the operation unit 55 or the like. Here, there is also a case where the provisional tumor is not reflected in the ultrasound image, but in the following, for convenience, a case where the provisional tumor is reflected in the ultrasound image will be described.

Therefore, in step S18, the CPU 51 waits until the above-described instruction information is input, and in step S20, the CPU 51 acquires a size of the provisional tumor in the horizontal direction and the longitudinal direction (hereinafter, referred to as "size during compression") and stores the acquired size in the storage unit 52. In the present embodiment, a size during the compression of the provisional tumor is acquired by the CPU 51 by causing the user to designate the position of each of end points of the provisional tumor in the horizontal direction and the vertical direction with respect to the ultrasound image displayed on the display 54 at this point in time, and deriving a distance between the designated positions. However, the present disclosure is not limited to this form, and for example, a form may be adopted in which the CPU 51 automatically acquires the size during the compression by extracting the provisional tumor from the ultrasound image displayed on the display 54 at this point in time by using pattern matching, an image extraction model that has been machine-learned in advance, or the like, and deriving the size during compression.

In step S22, with respect to the image generation apparatus 10, the CPU 51 performs control (hereinafter, referred to as "decompression") of releasing the compressed state by the compression member 40 and changing the compression pressure on the target breast to a predetermined lower limit value. By this decompression, the compression pressure of the compression member 40 on the target breast is gradually reduced from the compression pressure (50 N in present embodiment) indicated by the setting information to the lower limit value compression pressure (20 N in present embodiment).

Therefore, in step S24, the CPU 51 waits until the decompression is terminated, and in step S26, the CPU 51 acquires the size (hereinafter, referred to as "size during decompression") of the provisional tumor at this point in time in the same manner as that of processing in step S20.

In step S28, the CPU 51 determines whether or not the provisional tumor is the tumor as described above by using the size during the compression and the size during the decompression, and in a case of affirmative determination, the process proceeds to step S30. In the present embodiment, in a case where a difference between a size in the horizontal direction among sizes during the compression and a size in the horizontal direction among sizes during the decompression is equal to or less than a predetermined threshold value (for example, 0.5 mm), it is determined that the provisional tumor is a tumor, but the present disclosure is not limited thereto. For example, a form may be adopted in which it is determined that the provisional tumor is a tumor in a case where a difference between a size in the vertical direction among sizes during the compression and a size in the vertical direction among sizes during the decompression is equal to or less than the threshold value.

In step S30, the CPU 51 determines whether or not the size (in present embodiment, larger size out of size in horizontal direction and size in vertical direction) during the compression is equal to or larger than a predetermined size, and in a case of affirmative determination, the process proceeds to step S32. In the present embodiment, the size during the compression in a case where the size during the non-compression is set to be equal to or more than 5 mm and a maximum value of the correction coefficient is set to 1.2 is assumed as the predetermined size, where 4.17 mm (=5/1.2) is applied. However, it is needless to say that the present invention is not limited to this form.

In step S32, the CPU 51 executes processing of correcting the size during the compression to the size during the non-compression. In this case, the CPU 51 reads out a correction coefficient of each of the horizontal direction and the vertical direction corresponding to the compression pressure and the compression thickness indicated by the setting information, that is, the compression pressure and the compression thickness in a case where the size during the compression is acquired, from the correction coefficient database 52B. Then, the CPU 51 derives a size of the tumor after correction, that is, the size of the tumor during the non-compression, by multiplying the corresponding correction coefficient for each of the size in the horizontal direction and the size in the vertical direction in the size during the compression.

Figure 10:
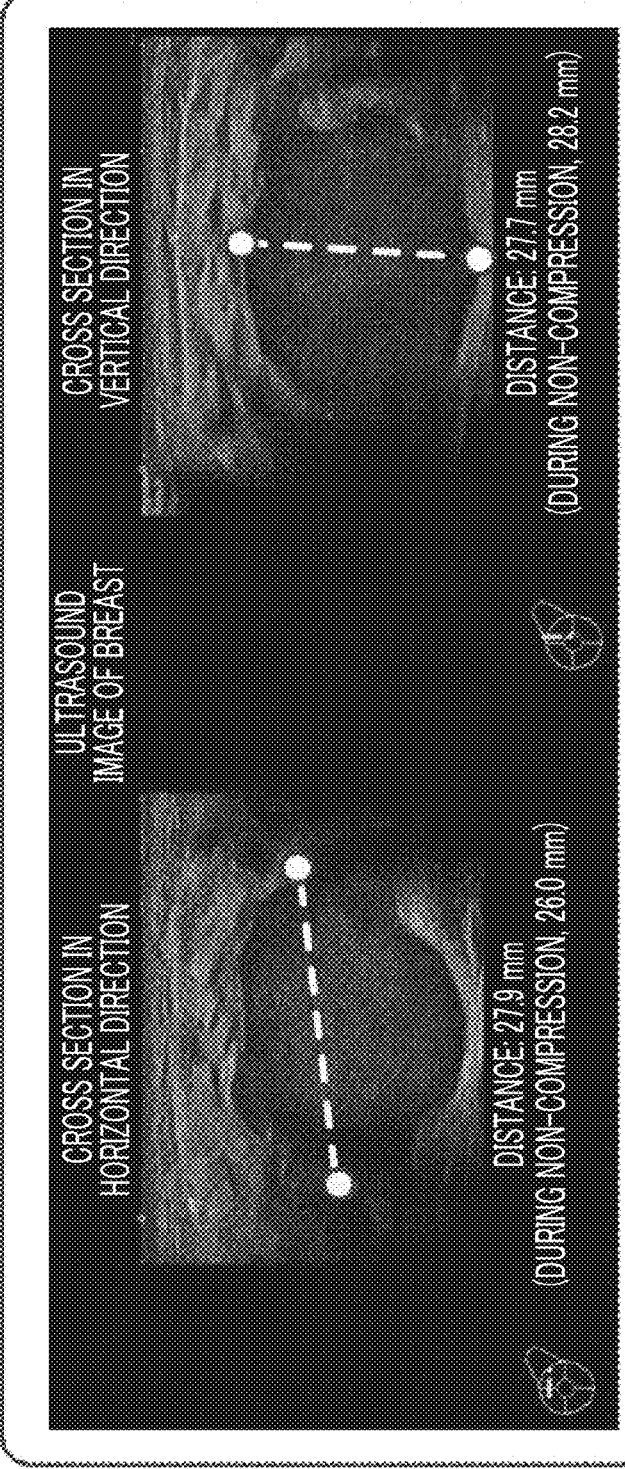
FIG. 10 is a photograph showing an example of a first size display screen according to the embodiment.

In step S34, the CPU 51 controls the display 54 to display a first size display screen having a predetermined configuration using the size during the compression and the size of the tumor during the non-compression derived by the processing of step S32, and then the process proceeds to step S38. FIG. 10 shows an example of the first size display screen according to the present embodiment.

As shown in FIG. 10, in the first size display screen according to the present embodiment, the ultrasound image (in example shown in FIG. 10, both cross-sectional images in horizontal direction and vertical direction) at the point in time at which the decompression is terminated is displayed. In addition, in the first size display screen according to the present embodiment, the size during the compression and the size of the tumor after the correction by the correction coefficient, that is, the size of the tumor during the non-compression are displayed separately in each of the horizontal direction and the vertical direction. In FIG. 10, the size during the compression is displayed as "distance".

As shown in FIG. 10, the size of the tumor during the non-compression is a smaller value than the size during the compression for the size in the horizontal direction, and is a larger value than the size during the compression for the size in the vertical direction.

Figure 11:
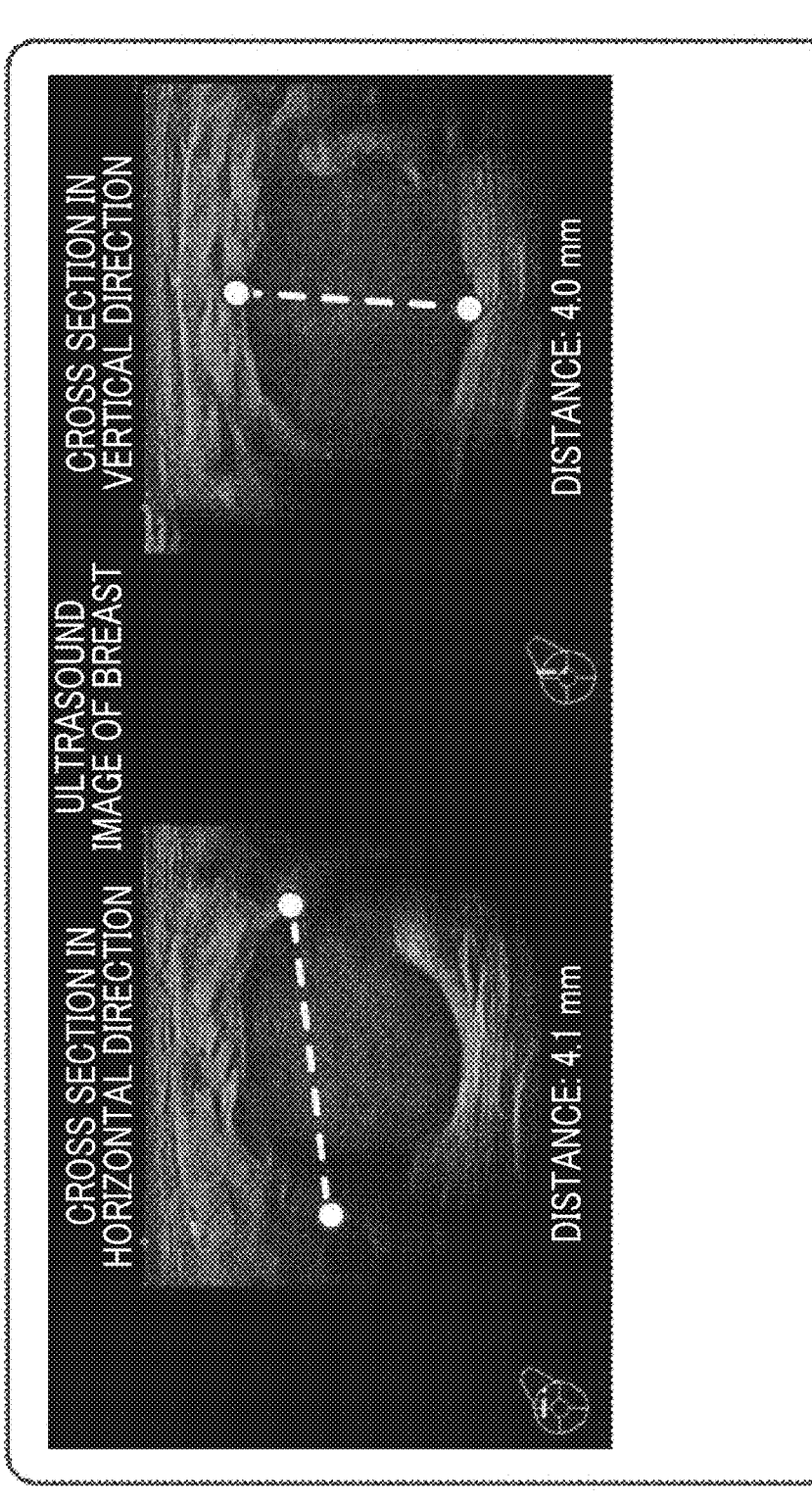
FIG. 11 is a photograph showing an example of a second size display screen according to the embodiment.

On the other hand, in a case where negative determination is made in step S28 or a case where negative determination is made in step S30, the process proceeds to step S36, the display 54 is controlled to display the second size display screen having a predetermined configuration, and then the process proceeds to step S38. FIG. 11 shows an example of the second size display screen according to the present embodiment.

As shown in FIG. 11, in the second size display screen according to the present embodiment, the ultrasound image (in example shown in FIG. 11, cross-sectional images in horizontal direction and vertical direction) at the point in time at which the decompression is terminated is displayed. In addition, in the second size display screen according to the present embodiment, a common tumor size during the compression and the non-compression is displayed separately in each of the horizontal direction and the vertical direction. In FIG. 11, the common tumor size is displayed as "distance".

As shown in FIG. 11, in a case where the provisional tumor is the tumor, the size of the tumor displayed on the second size display screen is a value smaller than the above-described threshold value (in present embodiment, 4.17 mm). In FIGS. 10 and 11, the ultrasound images are referred to as the same image for convenience, but are actually different images.

In step S38, the CPU 51 executes the category classification support processing described above, and then terminates the present information processing.

As described above, the console 50 as the information processing apparatus according to the present embodiment comprises the estimation unit 60 that estimates, in a case where capturing of a radiation image and an ultrasound image is performed for a breast in a state of being compressed by a compression member, a property related to a lesion of the breast during non-compression by the compression member, based on a measurement result for the lesion in the state in which the breast is compressed by the compression member. Therefore, processing using a difference in properties of lesions during the compression and the non-compression by the compression member can be performed.

In addition, with the console 50 according to the present embodiment, the size of the lesion in a state in which the breast is compressed by the compression member is applied as the above-described measurement result, and the size of the lesion during the non-compression is applied as the above-described property. Therefore, the difference in the properties of the lesions during the compression and the non-compression by the compression member can be used to estimate the size of the lesion during the non-compression from the size of the lesion during the compression.

In addition, with the console 50 according to the present embodiment, in a case where the lesion is a tumor, the processing of supporting the category classification of the tumor is executed by using the estimated size of the tumor during the non-compression. Therefore, the category classification of the tumor can be performed more simply as compared with a case where the size of the tumor during the non-compression is sequentially measured and input.

In addition, with the console 50 according to the present embodiment, in a case where the size of the lesion is equal to or larger than a predetermined threshold value, the estimation of the size of the lesion during the non-compression is performed. Therefore, estimation of a size of an unnecessary lesion can be avoided.

In addition, with the console 50 according to the present embodiment, as the measurement result, the measurement result of how the lesion is deformed by changing the compression pressure by the compression member is applied, and as the property, the state indicating whether or not the lesion is the liquid is applied. Therefore, it is possible to estimate whether the provisional tumor is a tumor or a liquid by using the deformation of the lesion in accordance with the change in the compression pressure by the compression member.

Further, with the console 50 according to the present embodiment, the change in the above-described compression pressure is performed at a position in which the lesion is suspected. Therefore, it is possible to more accurately estimate whether the provisional tumor is a tumor or a liquid.

Second Embodiment

In the first embodiment, the example of the form in a case where the size of the lesion during the non-compression is estimated by using the correction coefficient is described. In the second embodiment, an example of a form in a case where the size of the lesion during the non-compression is estimated in accordance with the state of the change in the size of the lesion in a case where the decompression is performed will be described. That is, the estimation unit 60 according to the present embodiment measures how the tumor deforms by changing the compression pressure by the compression member 40, and estimates the size of the lesion during the non-compression by using the deformation.

Figure 12:
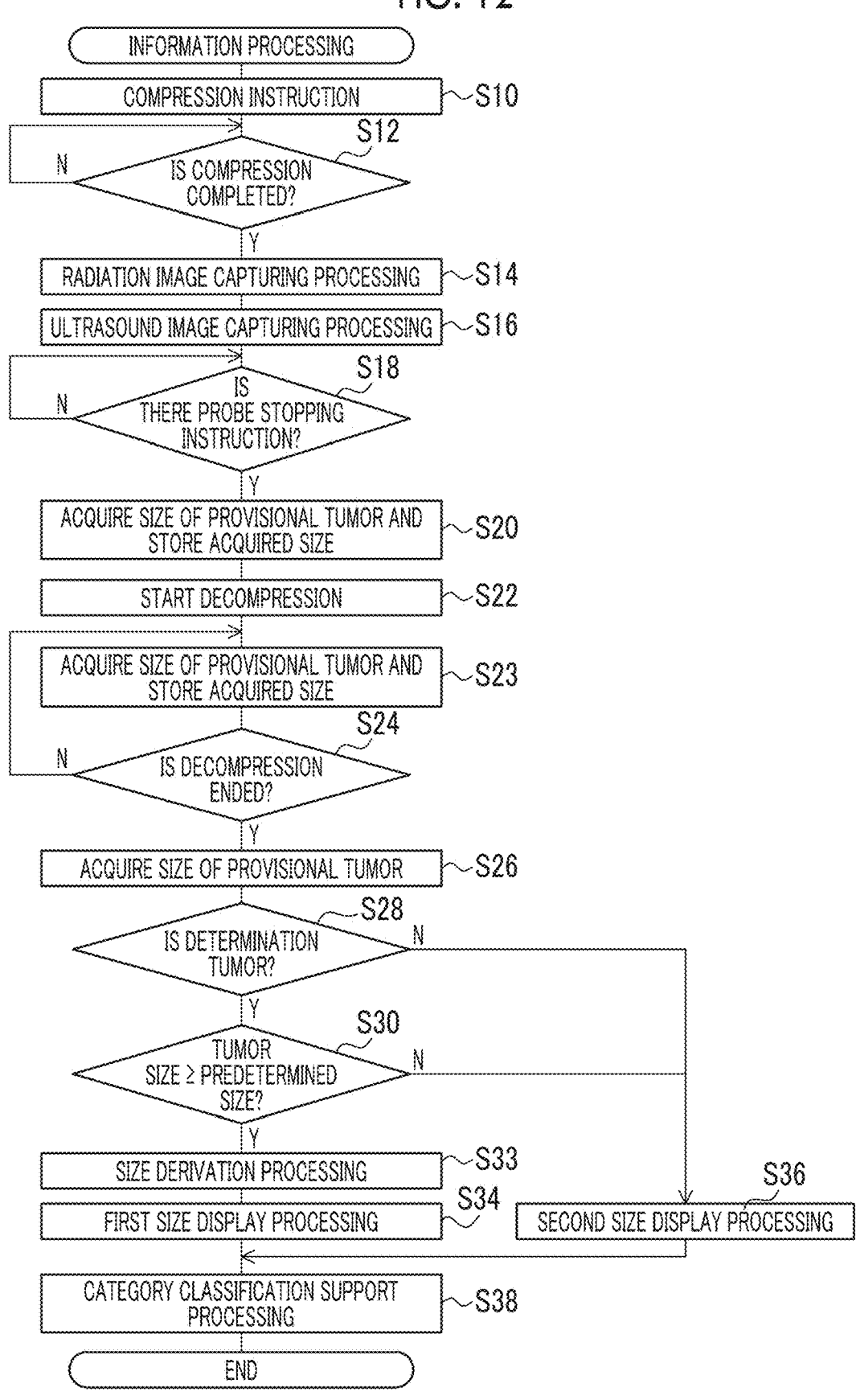
FIG. 12 is a flowchart showing an example of information processing according to a second embodiment.

Since the configuration of the image generation system 1 according to the present embodiment is substantially the same as the configuration of the image generation system 1 according to the first embodiment, an action in a case where the information processing of the console 50 according to the present embodiment is executed will be described below with reference to FIG. 12. FIG. 12 is a flowchart showing an example of the information processing according to the present embodiment. Among each step shown in FIG. 12, steps of performing the same processing as that shown in FIG. 9 are denoted by the same reference numerals as that in FIG. 9, and the description thereof will not be shown. In addition, hereinafter, in order to avoid the complication, a case where only the size in the horizontal direction is applied as the estimation target of the size of the tumor during the non-compression will be described, but the same applies to the estimation of the size in the vertical direction.

The information processing according to the present embodiment is different from the information processing according to the first embodiment only in that the processing of step S23 is added to the information processing according to the first embodiment, and the processing of step S33 is applied instead of the processing of step S32.

Figures 13, 14:
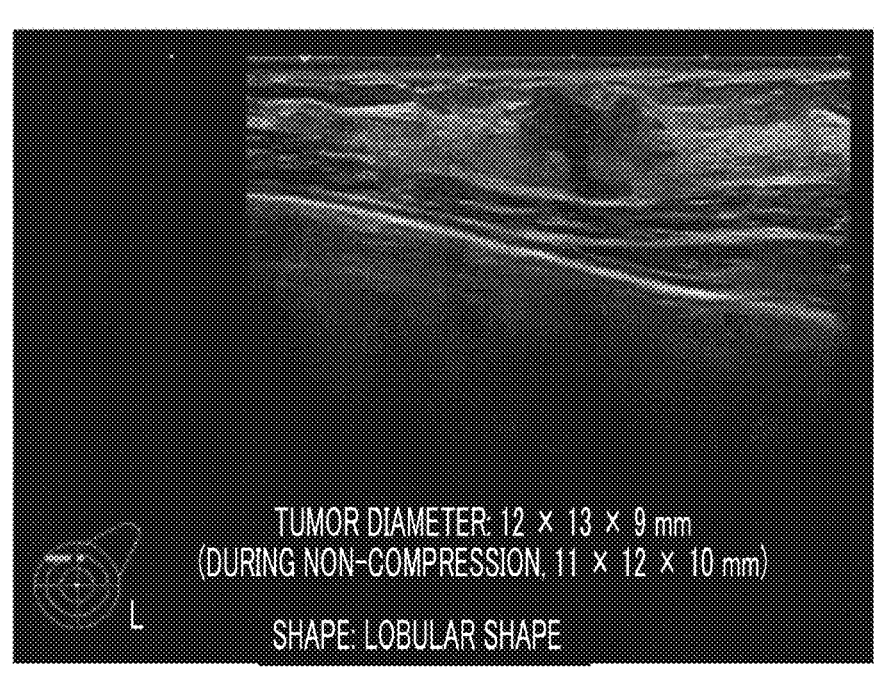
FIG. 13 is a diagram showing a description of a method of deriving a size of a tumor during non-compression according to the second embodiment, and is a diagram showing an example of a storage result of the size of the tumor in a case where a compression pressure is reduced by the compression member.
FIG. 14 is a photograph showing an example of a first size display screen according to a modification example of the embodiment.

That is, in step S23, the CPU 51 acquires the size of the provisional tumor at this point in time (in present embodiment, size in horizontal direction) in the same manner as that in the processing of step S20 described above, and stores the size in the storage unit 52 together with the corresponding compression pressure. As this processing is repeatedly executed while the decompression is performed, as shown in FIG. 13 as an example, the storage unit 52 stores the compression pressure and the size of the provisional tumor in the horizontal direction for each predetermined period in a time series from the start of the decompression to the end of the decompression in the storage unit 52.

It should be noted that, in a case where the decompression is performed, the ultrasound image itself also enters defective from the middle of the decompression due to the poor adhesion between the breast and the compression member 40. The example shown in FIG. 13 is an example in a case where the compression pressure is changed from 50 N to 20 N in the decompression. In the example shown in FIG. 13, the ultrasound image can also be obtained normally until the compression pressure reaches 30 N, so that the size of the provisional tumor can be acquired, but the size of the provisional tumor cannot be obtained in a case where the compression pressure reaches 20 N.

Then, in step S33, the CPU 51 reads out all the compression pressures and the sizes of the provisional tumors stored in the storage unit 52, and uses these pieces of information to estimate the size of the tumor during the non-compression. That is, in the example shown in FIG. 13, it can be seen that the size of the provisional tumor is reduced by 0.1 mm each time the compression pressure is reduced by 10 N, and the compression pressure and the size of the provisional tumor have a proportional relationship. In this case, the CPU 51 estimates the size of the tumor during non-compression, that is, in a case where the compression pressure reaches 0, as 10.0 mm as a result of decreasing the size of the provisional tumor by 0.1 mm each time the compression pressure is decreased by 10 N.

As described above, with the console 50 according to the present embodiment, the measurement result of how the lesion deforms by changing the compression pressure by the compression member is applied as the measurement result, and the size of the lesion during the non-compression is applied as the property. Therefore, in the present embodiment, the size of the lesion can be estimated by using the deformation of the lesion in accordance with the change in the compression pressure.

It should be noted that, in each of the above-described embodiments, a case is described where the CPU 51 provided in the console 50 is applied as the processor according to the technology of the present disclosure, but the present disclosure is not limited thereto. For example, a form may be adopted in which a CPU of the controller 20 provided in the image generation apparatus 10 is applied as the processor according to the technology of the present disclosure.

In addition, in the first embodiment, a case where a two-dimensional size in the horizontal direction and the vertical direction is applied as the size of the lesion has been described, but the present disclosure is not limited thereto. For example, a form may be adopted in which, in addition to the horizontal direction and the vertical direction, a three-dimensional size in the depth direction, that is, a size in three directions intersecting each other is applied as the size of the lesion.

FIG. 14 shows an example of the first size display screen according to this form. As shown in FIG. 14, in this form, the size of the tumor during the compression and the size of the tumor after the correction by the correction coefficient, that is, the size of the tumor during the non-compression are displayed separately in each of the horizontal direction, the vertical direction, and the depth direction. In FIG. 14, the size of the tumor during the compression is displayed as "tumor diameter", and the size in each direction is displayed as the size in the horizontal direction×the size in the depth direction×the size in the vertical direction.

As shown in FIG. 14, the size of the tumor during the non-compression is a smaller value as compared with the size during the compression for the size in the horizontal direction and the depth direction, and is a larger value as compared with the size during the compression for the size in the vertical direction.

In addition, in the first embodiment, a case where a method of estimating the size of the lesion during the non-compression by using the correction coefficient in accordance with the compression pressure and the compression thickness is applied as a method of estimating the size of the lesion during the non-compression has been described, but the present disclosure is not limited thereto. For example, a form may be adopted in which the size of the lesion during the non-compression is estimated by using a simpler correction coefficient in accordance with only the compression pressure.

FIG. 15 is a schematic diagram showing an example of the configuration of the correction coefficient database 52B according to this form. As shown in FIG. 15, in this form, the correction coefficient is registered in advance in association with only the compression pressure. Therefore, according to this form, the size of the lesion during the non-compression can be estimated in a simpler and shorter time as compared with the console 50 according to the first embodiment.

In addition, in the first embodiment, a case is described where the size of the lesion during the non-compression is estimated by an operation using the correction coefficient, but the present disclosure is not limited thereto. For example, a form may be adopted in which the size of the lesion during the non-compression is estimated by table conversion using a table in which the size of the lesion during the compression and the size of the lesion during the non-compression are associated with each other to be registered.

In addition, in each of the above-described embodiments, a case is described in which the ultrasound probe 30 is automatically moved in a case of generating the ultrasound image, but the present disclosure is not limited thereto. For example, a form may be adopted in which a known probe in the related art, such as a one-dimensional probe or a two-dimensional probe, is applied instead of the ultrasound probe 30, and a person manually moves the ultrasound probe to generate the ultrasound image.

In addition, in each of the above-described embodiments, a case where the state indicating the size of the lesion and whether or not the lesion is a liquid is applied as the property of the technology of the present disclosure has been described, but the present disclosure is not limited thereto. For example, a form may be adopted, in which clarity of a boundary portion of the lesion, variation in contrast of an internal structure of the lesion, an aspect ratio of the size of the lesion in the horizontal direction, the vertical direction, and the depth direction, or the like is applied as the properties of the technology of the present disclosure. Here, as an example, in the variation of the contrast, because the cyst is a liquid and thus tends to be uniform, while the tumor is cellular and thus tends to be non-uniform, this point is used to estimate whether the lesion is a liquid (cyst) or a tumor. In addition, regarding an asbestos ratio, the higher the asbestos ratio, the higher the possibility that the tumor is malignant, and this point is used to estimate the possibility.

It should be noted that, in each of the above-described embodiments, for example, as a hardware structure of a processing unit that executes various types of processing, such as the estimation unit 60, the processing execution unit 62, and the display controller 64, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured with one of the various types of processors, or a combination of two or more processors of the same type or different types (for example, a combination of a plurality of FPGAs, or a combination of a CPU and an FPGA). Further, a plurality of processing units may be configured with one processor.

As an example of configuring a plurality of processing units with one processor, first, there is a form in which, as typified by computers such as a client and a server, one processor is configured by combining one or more CPUs and software, and the processor functions as a plurality of processing units. A second example is a form of using a processor that realizes the function of the entire system including the plurality of processing units by one integrated circuit (IC) chip, as represented by a system on chip (SoC) or the like. As described above, the various types of processing units are configured using one or more of the various types of processors as a hardware structure.

Further, the hardware structure of these various processors is, more specifically, an electric circuit (circuitry) in which circuit elements such as semiconductor elements are combined.

In addition, in each of the above-described embodiments, the aspect is described in which the information processing program 52A is stored (installed) in the storage unit 52 of the console 50 in advance, but the present disclosure is not limited thereto. The information processing program 52A may be provided in a form of being recorded in a recording medium, such as a compact disc read only memory (CD-ROM), a digital versatile disc read only memory (DVD-ROM), and a universal serial bus (USB) memory. In addition, a form may be adopted in which the information processing program 52A is downloaded from an external apparatus via the network.

From the above description, the invention described in the following additional notes can be understood.

Additional Note 1

An information processing apparatus comprising: at least one processor, wherein the processor estimates, in a case where capturing of a radiation image and an ultrasound image is performed for a breast in a state of being compressed by a compression member, a property related to a lesion of the breast during non-compression by the compression member, based on a measurement result for the lesion in the state in which the breast is compressed by the compression member.

Additional Note 2

The information processing apparatus according to appendix 1, wherein the measurement result is a size of the lesion in the state in which the breast is compressed by the compression member, and the property is a size of the lesion during the non-compression.

Additional Note 3

The information processing apparatus according to appendix 2, wherein the processor executes, in a case where the lesion is a tumor, processing of supporting category classification of the tumor by using the estimated size of the tumor during the non-compression.

Additional Note 4

The information processing apparatus according to appendix 2 or appendix 3, wherein the processor estimates the size of the lesion during the non-compression in three directions intersecting with each other.

Additional Note 5

The information processing apparatus according to any one of appendixes 2 to 4, wherein the processor performs, in a case where the size of the lesion is equal to or larger than a predetermined threshold value, estimation of the size of the lesion during the non-compression.

Additional Note 6

The information processing apparatus according to appendix 1, wherein the measurement result is a measurement result of how the lesion is deformed by changing a compression pressure by the compression member, and the property is at least one of a size of the lesion during the non-compression or a state indicating whether or not the lesion is a liquid.

Additional Note 7

The information processing apparatus according to appendix 6, wherein the change in the compression pressure is performed at a position in which the lesion is suspected.

Additional Note 8

An image generation system comprising: the information processing apparatus according to any one of appendixes 1 to 7; and an image generation apparatus that generates an image used in the information processing apparatus.

Additional Note 9

A program causing a computer to execute a process comprising: estimating a property related to a lesion of the breast during non-compression by a compression member, based on a measurement result for the lesion in a state in which the breast is compressed by the compression member, in a case where capturing of a radiation image and an ultrasound image is performed for the breast the state of being compressed by the compression member.

What is claimed is:

1. An information processing apparatus comprising:
   at least one processor,
   wherein the processor estimates, in a case where capturing of a radiation image and an ultrasound image is performed for a breast in a state of being compressed by a compression member, a property related to a lesion of the breast during non-compression by the compression member, based on a measurement result for the lesion in the ultrasound image captured while the breast is compressed by the compression member.

2. The information processing apparatus according to claim 1,
   wherein the measurement result is a size of the lesion in the state in which the breast is compressed by the compression member, and
   the property is a size of the lesion during the non-compression.

3. The information processing apparatus according to claim 2,
   wherein the processor executes, in a case where the lesion is a tumor, processing of supporting category classification of the tumor by using the estimated size of the tumor during the non-compression.

4. The information processing apparatus according to claim 3,
   wherein the processor estimates the size of the lesion during the non-compression in three directions intersecting with each other.

5. The information processing apparatus according to claim 3,
   wherein the processor performs, in a case where the size of the lesion is equal to or larger than a predetermined threshold value, estimation of the size of the lesion during the non-compression.

6. The information processing apparatus according to claim 2,
   wherein the processor estimates the size of the lesion during the non-compression in three directions intersecting with each other.

7. The information processing apparatus according to claim 2,
   wherein the processor performs, in a case where the size of the lesion is equal to or larger than a predetermined threshold value, estimation of the size of the lesion during the non-compression.

8. The information processing apparatus according to claim 1,
   wherein the measurement result is a measurement result of how the lesion is deformed by changing a compression pressure by the compression member, and
   the property is at least one of a size of the lesion during the non-compression or a state indicating whether or not the lesion is a liquid.

9. The information processing apparatus according to claim 8,
   wherein the change in the compression pressure is performed at a position in which the lesion is suspected.

10. An image generation system comprising:
   the information processing apparatus according to claim 1; and
   an image generation apparatus that generates an image used in the information processing apparatus.

11. A non-transitory computer-readable storage medium storing a program that causes a computer to execute a process, the process comprising:
   estimating a property related to a lesion of the breast during non-compression by a compression member, based on a measurement result for the lesion in an ultrasound image captured while the breast is compressed by the compression member, in a case where capturing of a radiation image and an ultrasound image is performed for the breast in a state of being compressed by the compression member.

* * * * *